(12) United States Patent
Kawasaki et al.

(10) Patent No.: US 8,600,720 B2
(45) Date of Patent: Dec. 3, 2013

(54) STIMULATING TASK PRESENTATION DEVICE AND STIMULATING TASK PRESENTATION METHOD FOR LIVING BODY OPTICAL MEASUREMENT APPARATUS

(75) Inventors: Shingo Kawasaki, Tokyo (JP); Noriyoshi Ichikawa, Tokyo (JP); Kiyoto Kasai, Tokyo (JP); Ryu Takizawa, Tokyo (JP); Yuki Kawakubo, Tokyo (JP); Ayaka Takahashi, Tokyo (JP); Hitoshi Kuwabara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 236 days.

(21) Appl. No.: 12/996,190

(22) PCT Filed: Jun. 3, 2009

(86) PCT No.: PCT/JP2009/060113
§ 371 (c)(1),
(2), (4) Date: Dec. 3, 2010

(87) PCT Pub. No.: WO2009/148069
PCT Pub. Date: Dec. 10, 2009

(65) Prior Publication Data
US 2011/0082677 A1    Apr. 7, 2011

(30) Foreign Application Priority Data
Jun. 4, 2008 (JP) .................................. 2008-146721

(51) Int. Cl.
*G06G 7/58* (2006.01)
(52) U.S. Cl.
USPC ........................................................... 703/11
(58) Field of Classification Search
USPC ........................................................... 703/11
See application file for complete search history.

(56) References Cited

U.S. PATENT DOCUMENTS

| | | | |
|---|---|---|---|
| 4,862,359 A * | 8/1989 | Trivedi et al. | 600/544 |
| 5,311,877 A | 5/1994 | Kishi | |
| 5,911,581 A | 6/1999 | Reynolds et al. | |
| 2004/0171919 A1 | 9/2004 | Maki et al. | |
| 2006/0206017 A1 | 9/2006 | Kawasaki et al. | |
| 2007/0083097 A1 | 4/2007 | Fujiwara et al. | |
| 2008/0262327 A1 | 10/2008 | Kato | |

FOREIGN PATENT DOCUMENTS

| | | |
|---|---|---|
| JP | 2004-261265 | 9/2004 |
| JP | 2006-187305 | 7/2006 |
| JP | 2007-54138 | 3/2007 |
| WO | WO 03/075762 A1 | 9/2003 |
| WO | WO2004/021889 | 3/2004 |
| WO | WO2006/009178 | 1/2006 |

OTHER PUBLICATIONS

European Search Report dated Aug. 20, 2013 for Application No. 09758336.3.

* cited by examiner

*Primary Examiner* — Jerry Lin
(74) *Attorney, Agent, or Firm* — Antonelli, Terry, Stout & Kraus, LLP.

(57) ABSTRACT

A load of a stimulating task on an examinee with a resting task being unstable is excluded, and an accurate answer of an examinee to presentation of a stimulating task is enabled. A stimulating task presentation device in a living body optical measurement device includes a stimulation presenting unit configured to present a stimulation to an examinee, a brain function measurement device for measuring a brain function of the examinee in parallel to presentation of the stimulation, and a stimulation presentation controller configured to control the stimulation presented by the stimulation presenting unit, and the stimulation presentation controller has a function of setting a resting task and a stimulating task to be presented to the examinee, a function of detecting an answer of the examinee to the resting task and the stimulating task, and a task presentation control function of determining the degree of stability on the basis of the detection result when the resting task is presented, and controlling presentation of the resting task or the stimulating task on the basis of the degree of stability.

13 Claims, 16 Drawing Sheets

FIG. 4A

| | |
|---|---|
| 1. BUTTON DETERMINATION | (1) RIGHT ANSWER RATE: COINCIDENCE RATE BETWEEN ARROW DIRECTION DISPLAYED ON SCREEN AND BUTTON (UP, DOWN, RIGHT, LEFT)<br>RIGHT ANSWER RATE = (CORRECT ANSWER/PRESENTATION FREQUENCY) × 100<br>(2) REACTION TIME: TIME FROM PRESENTATION OF ARROW ON SCREEN TILL PUSH OF BUTTON<br>REACTION TIME AVERAGE = TOTAL BUTTON PUSHING TIME/PRESENTATION FREQUENCY<br>REACTION TIME STANDARD DEVIATION<br>(3) REACTION FREQUENCY: BUTTON PUSHING FREQUENCY |
| 2. MICROPHONE DETERMINATION | (4) UTTERANCE SPEED: CALCULATE PERIOD [Hz] FROM TIME BETWEEN UTTERED WORDS<br>UTTERANCE SPEED = 1/UTTERANCE INTERVAL TIME<br>(5) MAGNITUDE OF UTTERANCE: CALCULATE MAGNITUDE OF UTTERANCE BY dB |

FIG. 4 C

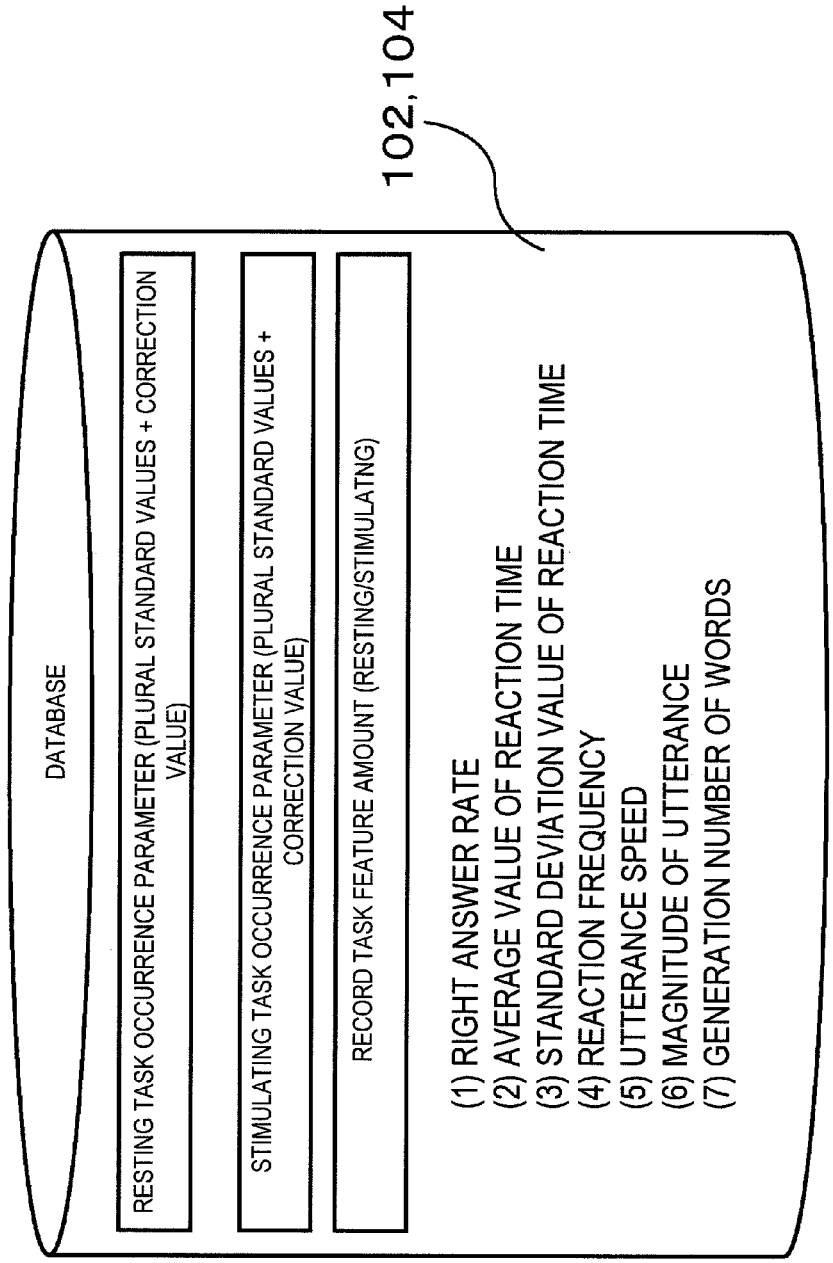

DATABASE

RESTING TASK OCCURRENCE PARAMETER (PLURAL STANDARD VALUES + CORRECTION VALUE)

STIMULATING TASK OCCURRENCE PARAMETER (PLURAL STANDARD VALUES + CORRECTION VALUE)

RECORD TASK FEATURE AMOUNT (RESTING/STIMULATING)

(1) RIGHT ANSWER RATE
(2) AVERAGE VALUE OF REACTION TIME
(3) STANDARD DEVIATION VALUE OF REACTION TIME
(4) REACTION FREQUENCY
(5) UTTERANCE SPEED
(6) MAGNITUDE OF UTTERANCE
(7) GENERATION NUMBER OF WORDS 102, 104

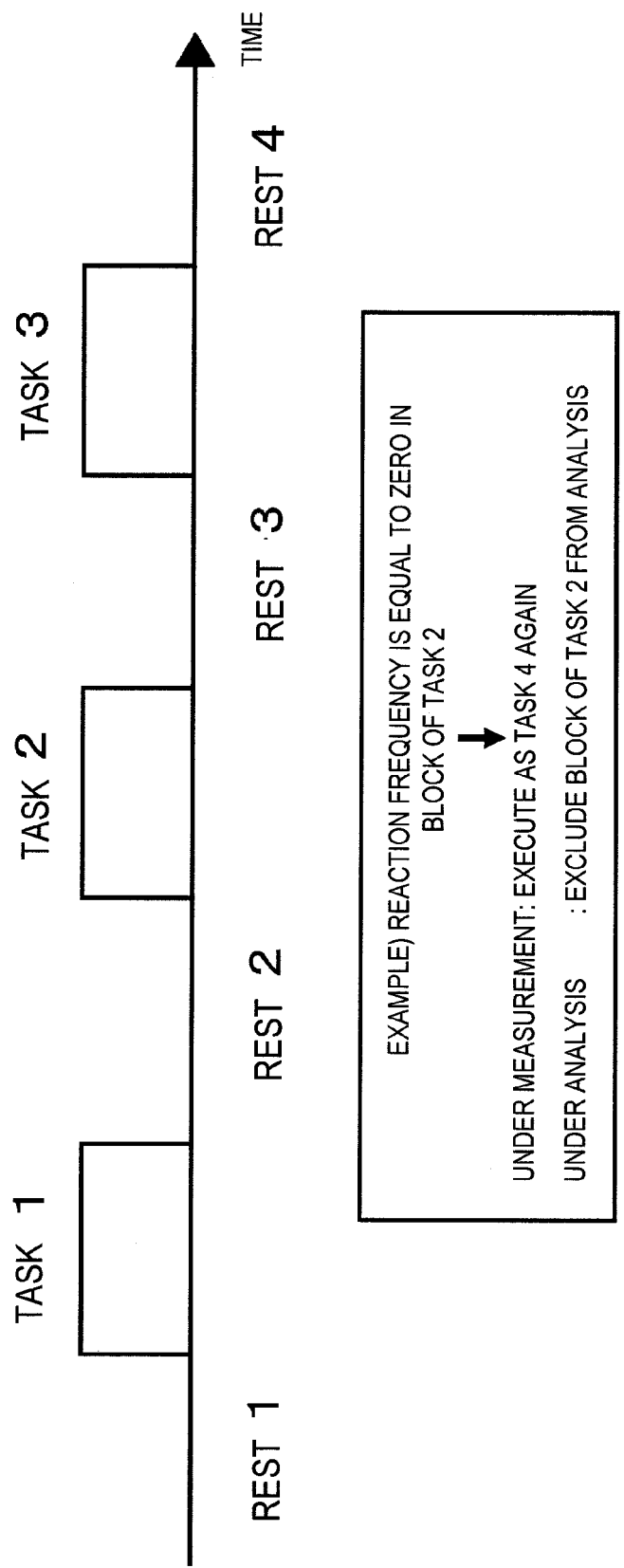

STIMULATING TASK PRESENTATION DEVICE AND STIMULATING TASK PRESENTATION METHOD FOR LIVING BODY OPTICAL MEASUREMENT APPARATUS

TECHNICAL FIELD

The present invention relates to a stimulating task presentation device and a stimulating task presentation method for a living body optical measurement apparatus.

BACKGROUND ART

A living body optical measurement apparatus is a device that can simply and easily measure blood circulation/hemodynamics and hemoglobin variation in a living body while placing an examinee under a little restraint and having no harmful influence on the living body. In general, many reports on measurements of the activation state of cerebral cortex occurring between a resting task (control task) and a stimulating task have been released with respect to a living body optical measurement apparatus.

For example, Non-patent Document 1 reports hemoglobin variation of cerebral cortex occurring between "repeat of insignificant utterance" (resting task) and word recall utterance (stimulating task).

Furthermore, Non-patent Document 2 reports hemoglobin variation of cerebral cortex when a button is pushed to load a suppressing task.

Patent Document 1 discloses a stimulation presentation device for measuring a brain function in which presenting stimulation and presenting time and timing thereof can be edited by using a behavioral response, a brain activity signal or other physiological variation indexes from an examinee in consideration of a problem that a stimulation pattern to be presented is uniformly determined irrespective of an examinee's characteristic or an examinee's state under measurement in conventional devices and thus optimum stimulation type and presentation time are not set for every examinee.

PRIOR ART DOCUMENT

Patent Document

Patent Document 1: JP-A-2007-54138

Non-Patent Document

Non-patent Document 1: "Suto T et al: MultiChannel Near-infrared spectroscopy in depression and schizophrenia: Cognitive brain activation Study. Biol Psychiatry 55: 501-511 2004"

Non-patent Document 2: "Martin J. Herrmann et al: Optical topography during a Go-NoGo task assessed with multi-Channel near-infrared spectroscopy: Behavioural Brain Research 160 (2005) 135-140"

SUMMARY OF THE INVENTION

Problem to be Solved by the Invention

According to the report of the Non-patent Document 1, repeat of utterance "aiueo"/control time are described as a resting task, and presentation initial letter/word recall number/stimulation time are described as a stimulating task. However, stability of the resting task is important in an actual examination. When no attention is paid to utterance speed (timing) and magnitude of voice, there is a case where an examinee (a person under examination) executes the resting task with rapid utterance or a loud voice and thus there is a problem that a stimulating task is presented with the resting task being unstable.

Furthermore, the Non-patent Document 2 describes repeat of a task that a button is pushed when O is displayed on a screen and the button is not pushed when X is displayed. Only O is displayed under a resting task, and both of O and X are displayed under a stimulating task. Actually, with respect to this examination, when no attention is paid to the button pushing reaction, there are a case where an examinee cannot concentrate on the task and thus a right answer rate is equal to zero and also a case where the examinee does not watch O X on the screen and hits the button repeatedly, so that the reaction time is abnormally short. Accordingly, there is a problem that the measurement is made with the resting task and the stimulating task being unstable.

In the Non-patent Document 2, the resting task and the stimulating task are executed separately from each other, and the difference between hemoglobin measurement waveforms of both the resting task and the stimulating task is calculated to obtain a result. However, there is a case where no proper result is obtained from unstable data as described above. Furthermore, there is also a problem that the separate execution of the resting task and the stimulating task induces time lag between measurements and thus the state of the examinee varies.

According to the Patent Document 1, a next presentation stimulation is changed in accordance with the examinee's reaction, however, it is not sufficiently considered whether the state of the examinee is stable, that is, the degree of stability of the resting task is not sufficiently considered.

An object of the invention is to provide a stimulating task presentation device and a stimulating task presentation method in a living body optical measurement apparatus that can exclude loading of a stimulating task on an examinee with a resting task being unstable, and measure an accurate response of an examinee to stimulating task presentation.

Means of Solving the Problem

A representative example of the invention is as follows. That is, a stimulating task presentation device in a living body optical measurement device comprises a stimulation presenting unit that presents a stimulation to an examinee, a brain function measuring device that measures a brain function of the examinee in parallel to the presentation of the stimulation, and a stimulation presentation controller that controls the stimulation presented by the stimulation presenting unit, wherein the stimulation presentation controller has setting means that sets a resting task and a stimulating task to be presented to the examinee, detecting means that detects a response of the examinee to the resting task and the stimulating task, and task presentation control means that determines the degree of stability on the basis of the detection result when the resting task is presented, and controls the presentation of the resting task or the stimulating task on the basis of the degree of stability.

Effect of the Invention

According to the invention, the stimulating task presentation and the end of the measurement can be performed after "stabilization of the state under resting task" is implemented. Accordingly, more proper measurement can be performed.

BRIEF DESCRIPTION OF THE DRAWINGS

FIG. 10A is a diagram showing the processing of the resting task and the stimulating task which is another embodiment of the invention.

MODE FOR CARRYING OUT THE INVENTION

The invention implements a system that measures an utterance reaction time and an utterance frequency under a resting task with respect to a word recall task on a real-time basis, and shifts/presents a stimulating task at the time point when the utterance reaction time and the utterance frequency satisfy threshold conditions (degree of stability). Furthermore, the invention implements a system that measures a button push right answer rate, a reaction time and a reaction frequency under a resting task with respect to a button push suppressing task on a real-time basis and sifts/presents to a stimulating task at the time when a right answer rate, a reaction time average value, a reaction time standard deviation and a reaction frequency satisfy threshold conditions (degree of stability). Furthermore, the invention implements a system that finishes the measurement at the time point when the above parameters are satisfied in a second resting task after the stimulating task is finished.

Embodiments of the invention will be described hereunder in detail.

First Embodiment

Figure 1:
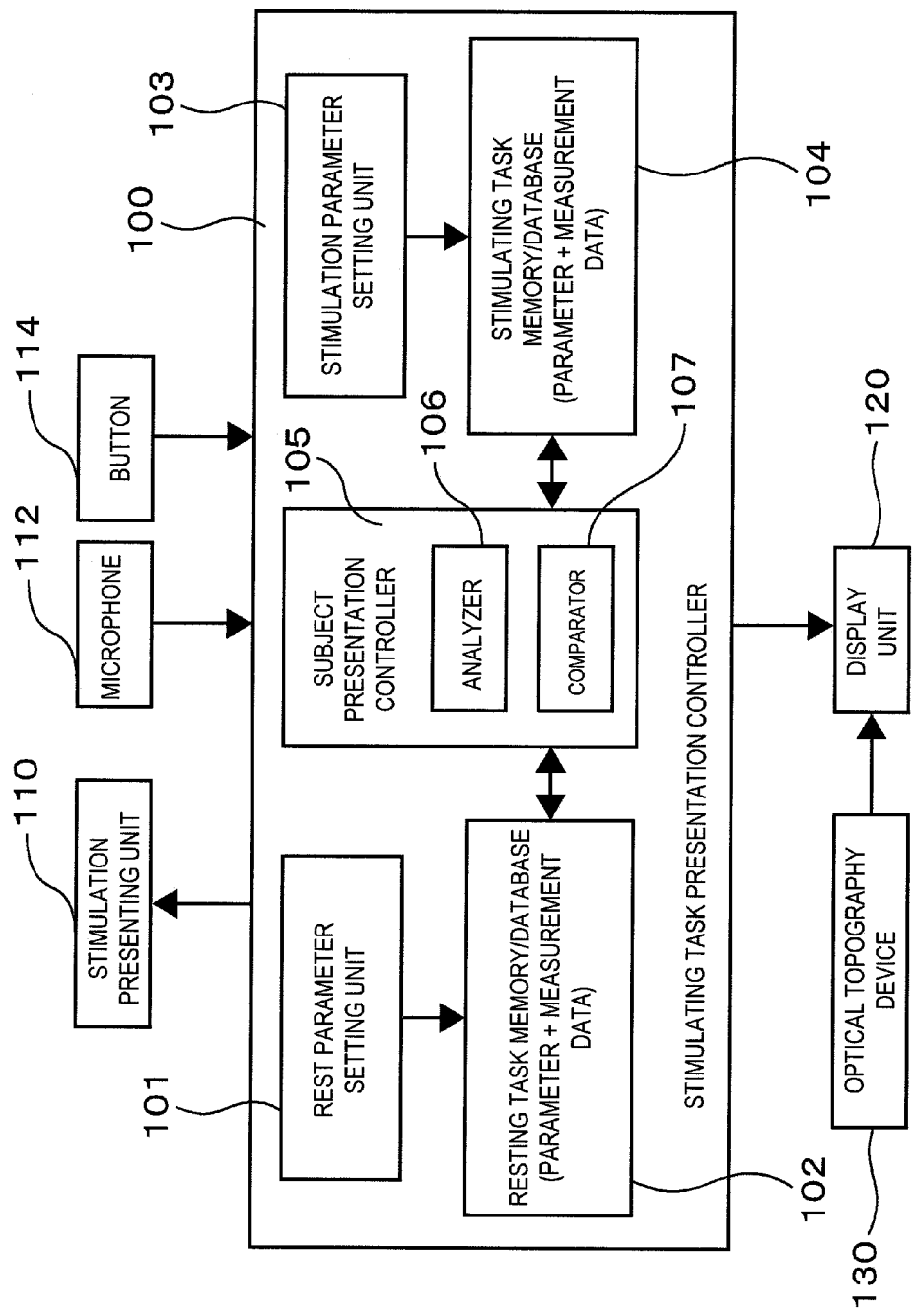
FIG. 1 is a functional block diagram showing a first embodiment of a living body optical measurement device in which a stimulating task presentation device of the invention is installed.
Figure 2:
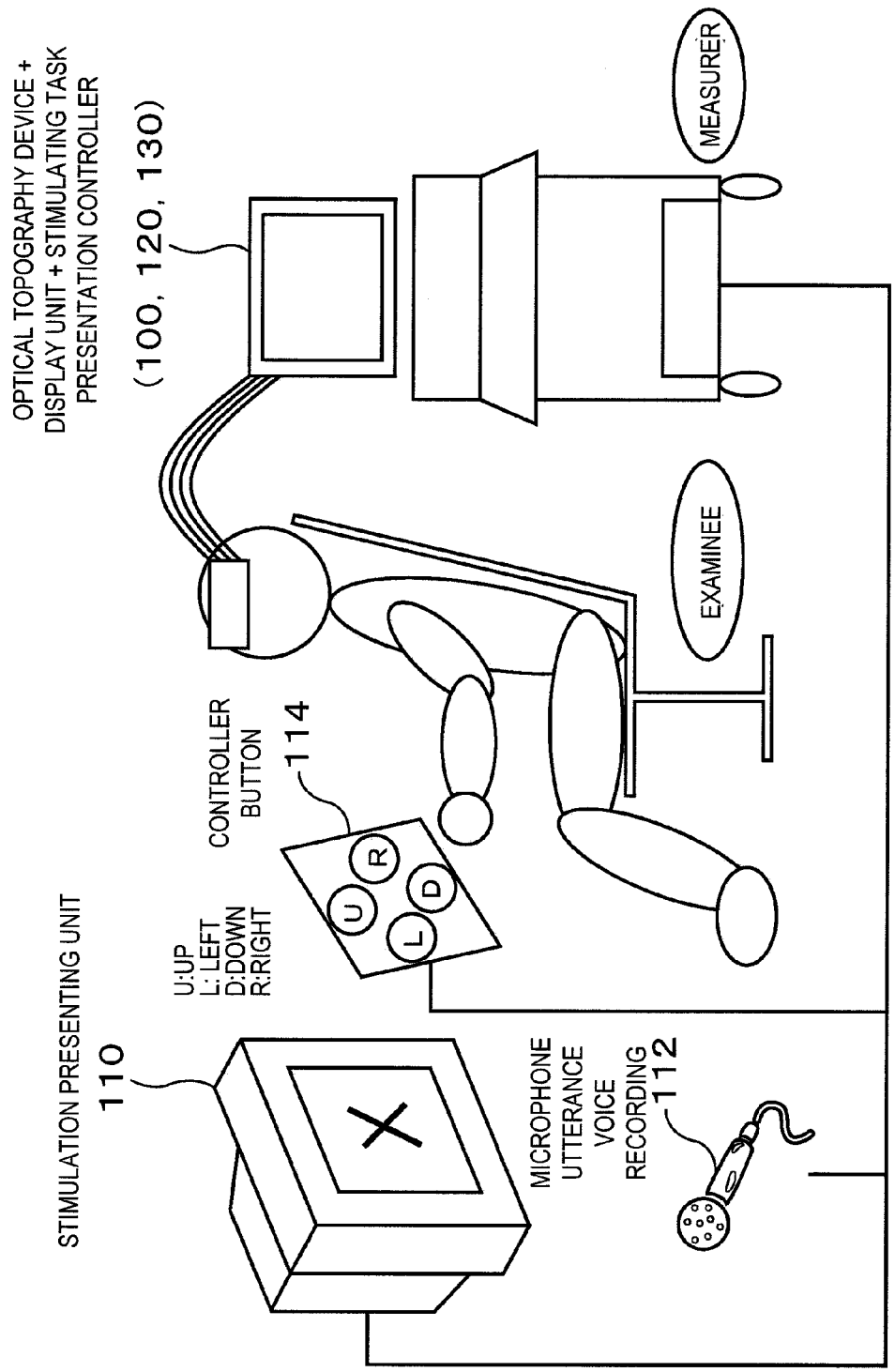
FIG. 2 is a diagram showing a scene of a measurement using a living body optical measurement device of this embodiment.

FIG. 1 is a functional block diagram showing a first embodiment in which a stimulating task presentation device is installed in a living body optical measurement device (optical topography device) of the invention, and FIG. 2 is a schematic diagram showing a measurement scene of the measurement device according to this embodiment. The device of this embodiment comprises a stimulating task presentation controller 100 for performing processing such as manual generation, presentation, analysis, etc. of a stimulating task, a stimulation presenting unit 110 for presenting a stimulation to an examinee by a monitor screen or the like, a microphone 112 serving as responding means from the examinee, a button 114, and a display unit 120 for displaying a processing result, etc. of the stimulating task presentation controller 100 for a measurer. An output of an optical topography device 130 for measuring a brain function is also displayed on the display unit 120.

The stimulating task presentation controller 100 has a rest parameter setting unit 101, a resting task memory/database 102, a stimulation parameter setting unit 103, a stimulating task memory/database 104 and a task presentation controller 105. The task presentation controller 105 has an analyzer 106 and a comparator 107. The optical topography device 130 has a function of irradiating an examinee (the head portion of a person under examination) with light having wavelength in the range from the visible region to the infrared region and detecting light of plural signals passing through the examinee by the same photodetector. The processing functions of the stimulating task presentation controller 100 and the optical topography device 130 are implemented by executing, through CPU, various programs loaded in a memory of a host computer or a personal computer connected to the host computer through a network. Furthermore, the input/output functions of the rest parameter setting unit 101, the stimulation parameter setting unit 103 and the display unit 120 are constructed by utilizing the user interface function of the display screen of the personal computer, for example.

The examinee is supplied with a stimulation from the stimulating task presentation controller 100 in parallel to the brain function measurement executed by the optical topography device 130, and a response to the stimulation is transmitted to the stimulating task presentation controller 100 through a response processing device such as the microphone 112 or the button 114. The stimulating task presentation controller 100 records a response result into the resting task memory/data base 102 or the stimulating task memory/data base 104

(hereinafter merely referred to as the data base of the stimulating task presentation controller 100 when discrimination is not particularly required).

FIG. 2 is a schematic diagram showing a measurement scene in the invention. For example, the examinee is supplied with a task of repeating an operation that the examinee pushes the controller button 114 when O is displayed on the stimulation presenting unit 110 and does not push the button when X is displayed. Only O is displayed under a resting task, and both of O and X are displayed under a stimulating task. Alternatively, the examinee is supplied with a task that the examinee pushes a predetermined same button under the resting task, and pushes a different button under the stimulating task. The timing at which the examinee pushes the button 114 of the controller is recorded as the reaction time and the reaction frequency in the database of the stimulating task presentation controller 100, and the coincidence between OX display on the monitor and push or non-push of the button is recorded as a right answer rate.

When the task is "microphone determination", the examinee is supplied with a repetitive task of utterance "a/i/u/e/o" as the resting task, for example, and a task of presentation initial letter/word recall number is supplied as the stimulating task. For example, the examinee is supplied with a task that the examinee utters a "a" contained word "ari, ame, . . . ". The uttered voice is recorded in the database of the stimulating task presentation controller 100 by the microphone 112, and an utterance reaction time and an utterance frequency are measured with the syllable between words being set as a breaking. The recorded reaction time, reaction frequency, right answer rate, etc. are displayed on the display unit 120 of the stimulating task presentation controller 100 on a real-time basis. Plural standard parameters are prepared as stimulating tasks in advance so that an optimum task can be selected in accordance with the age, using language, body condition, etc. of the examinee together with "button determination" and "microphone determination".

According to this embodiment, the degree of stability of the examinee under the resting task is calculated, and the processing shifts to the presentation of the stimulating task at a predetermined timing at which the degree of stability increases to a high value. For example, with respect to the word recall task using the microphone, the utterance reaction time and the utterance frequency under the resting task are measured on a real-time basis, and the shift to and presentation of the stimulating task are performed at the time point when the utterance reaction time and the utterance frequency satisfy the threshold conditions (degree of stability). Furthermore, with respect to the button push suppressing task using the button 114 of the controller, the button push right answer rate, reaction time and reaction frequency under the resting task are measured on a real-time basis, and the shift to and presentation of the stimulating task are performed at the time point when the right answer rate, the reaction time average value, the reaction time standard deviation and the reaction frequency satisfy the threshold conditions (degree of stability). Furthermore, with respect to the second resting task after the stimulating task is finished, the measurement is also finished at the time point when the above parameters are satisfied.

Figure 3:
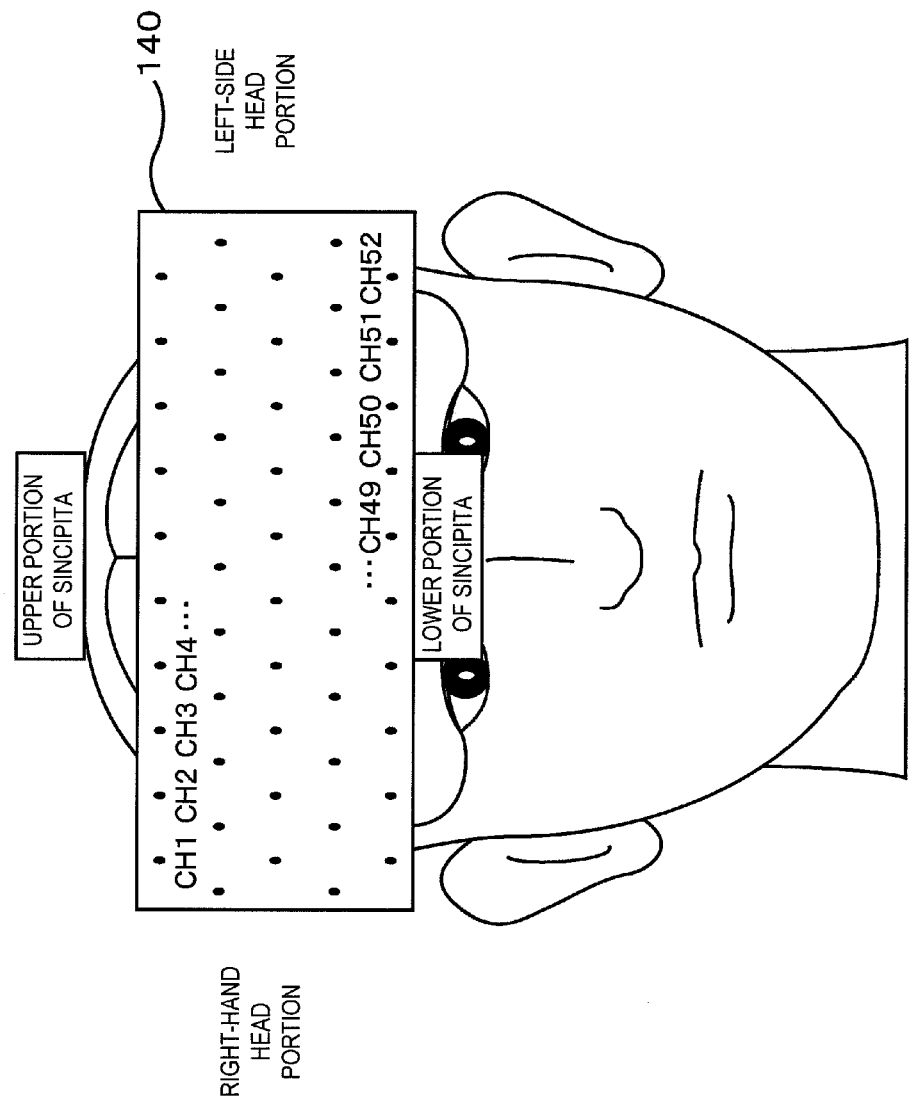
FIG. 3 is a diagram showing a measurement channel when light irradiator/detector as an example of an optical topography device used in the invention are disposed on an examinee (a frontal region of the examinee).

FIG. 3 is a diagram showing measurement channels (CH1 to CH52) when the light irradiator/detector 140 is disposed on the examinee (the frontal region of the person under examination) as an example of the optical topography device 130 used in the invention. In FIG. 3, light having a light intensity peak wavelength from the visible region to the near-infrared region in which light transmission to a living body is high is irradiated from the head portion of the examinee (person under examination), and the light is detected from a remote position. By arranging plural measurement points in a grid form, the variation of the light can be measured as an image. In connection with activation of a perceptual function or a motor function of a human, the blood amount of a cerebral cortex region serving to perform the function locally increases and thus the concentration of oxygenated hemoglobin or deoxygenated hemoglobin of the site concerned varies, so that the activity condition of the brain can be estimated.

Figure 4:
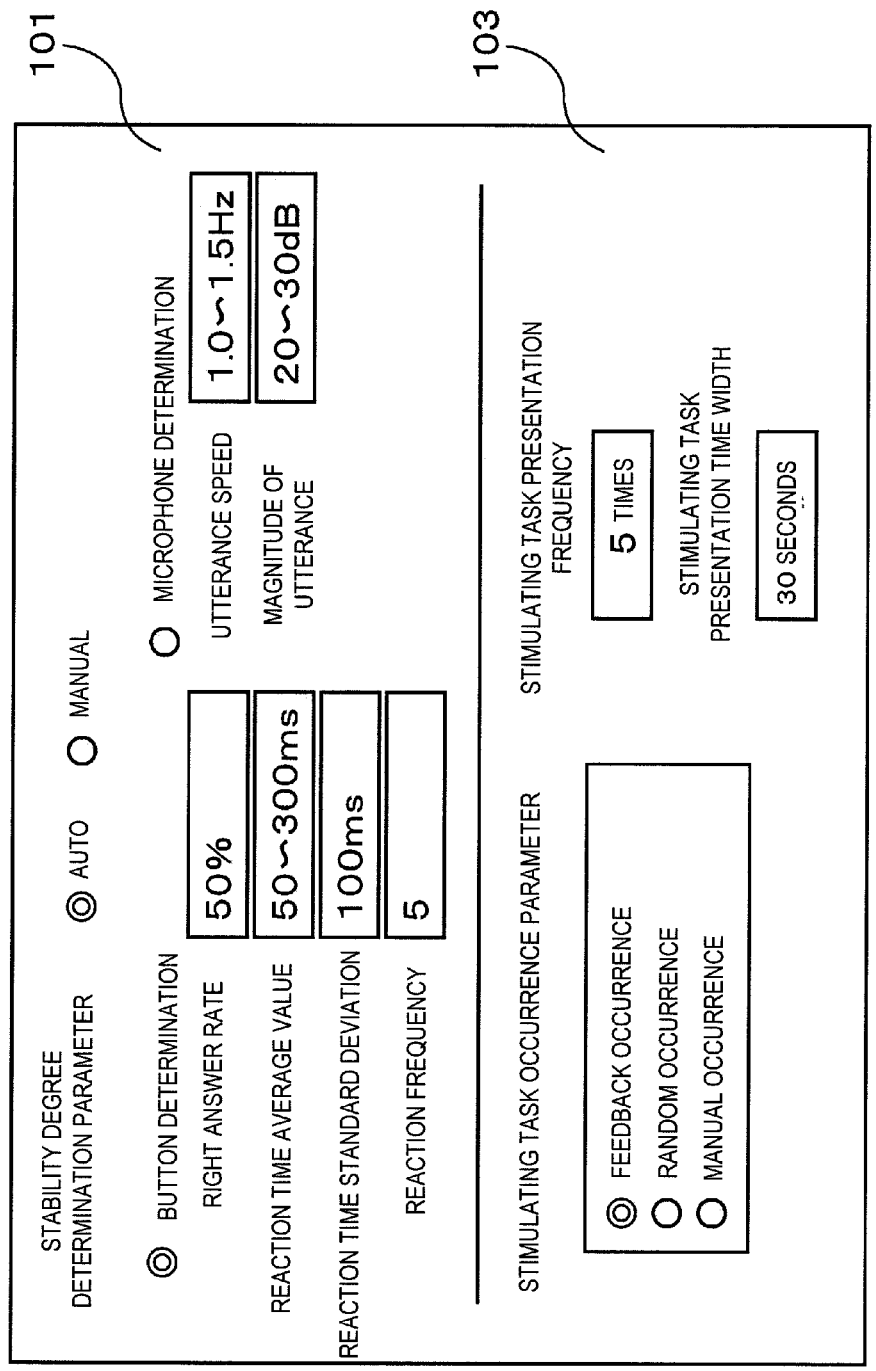
FIG. 4A is a table showing an example of a determination criterion of a resting state on the basis of "button determination", "microphone determination".
FIG. 4B is a diagram showing an example of an input/setting screen of various kinds of parameters in a rest parameter setting unit and a stimulation parameter setting unit of the stimulating task presentation device.
FIG. 4C is a diagram showing an example of information recorded in a database of the stimulating task presentation device.

FIG. 4A is a table showing an example of a determination criteria of the resting state based on "button determination", "microphone determination". When the resting task is "button determination", the examinee is supplied with a task of requiring a predetermined button operation, for example, and with respect to the right answer rate, response time and reaction frequency of the examinee at that time, threshold values are set as determination criteria on the basis of the criteria shown in the table. Furthermore, when the resting task is "microphone determination", the examinee is supplied with a task of repeating predetermined utterance, and with respect to the utterance speed and the utterance magnitude of the examinee at that time, threshold values are set as determination criteria on the basis of the criteria shown in the table.

FIG. 4B is a diagram showing an example of the input/setting screen of various kinds of parameters in the rest parameter setting unit 101 and the stimulation parameter setting unit 103 of the stimulating task presentation controller 100. FIG. 4C shows an example of information recorded in the databases 102, 104 of the stimulating task presentation controller 100.

Figure 5:
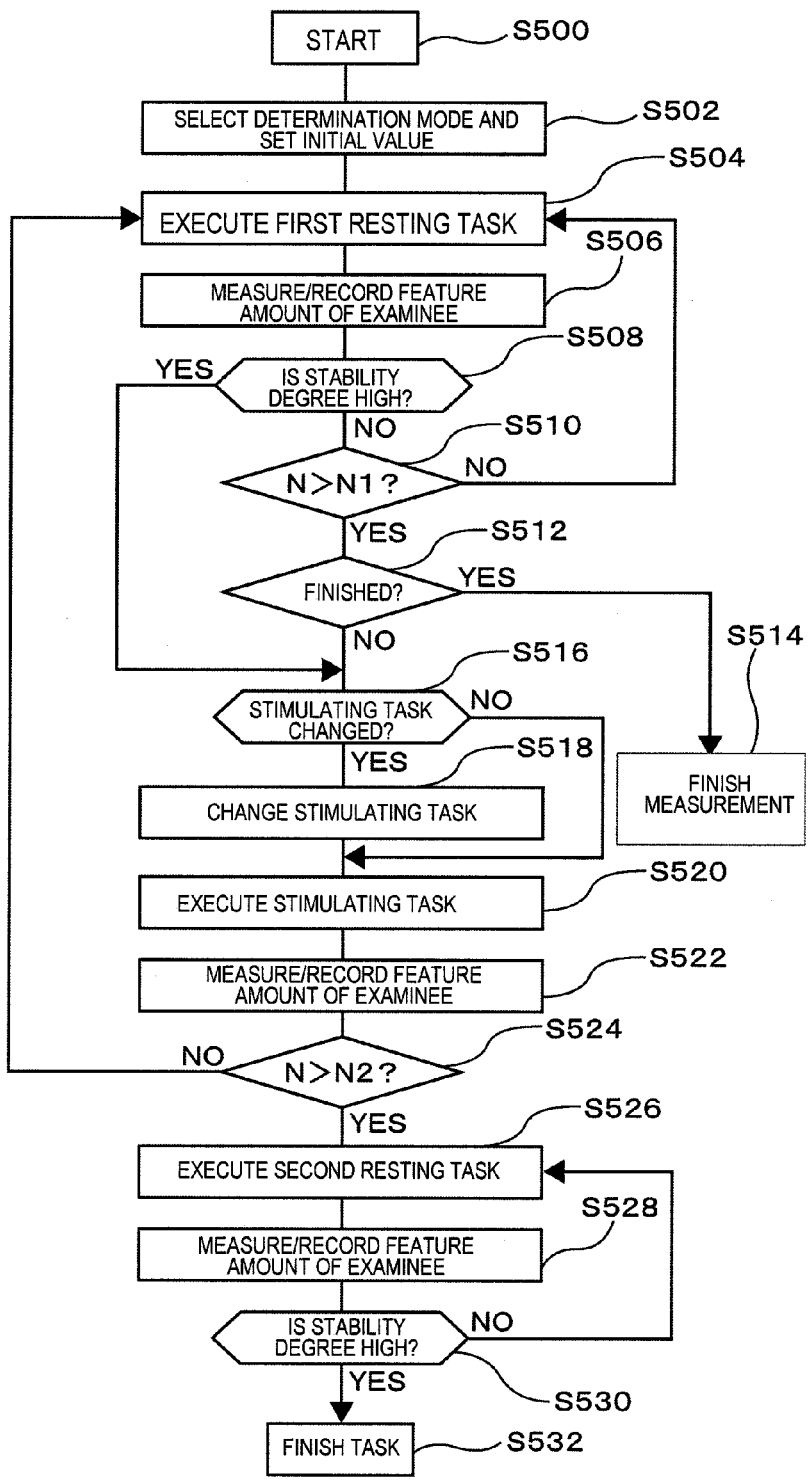
FIG. 5 is a diagram showing a flowchart of stimulating task presentation implementing "degree of state stability under resting task" in the first embodiment of the invention.

FIG. 5 is a flowchart showing the stimulating task presentation implementing "degree of state stability under resting task" in the first embodiment of the invention.

The operation of the measurement device according to the invention will be described along the above flowchart with reference to FIGS. 4A to 7.

First, the measurer sets a determination mode, threshold values for various types of tasks, a resting task repeat frequency N1 and a stimulating task repeat frequency N2 as initial values (S502). That is, initialization for various kinds of threshold values, etc. are performed on the input/setting screen of stability degree determining parameters of FIG. 4B, and the result is recorded in the databases 102, 104 of the stimulating task presentation controller 100.

For example, in the setting of the threshold values for the continuous shift from the resting task to the stimulating task, when the shift determination is automatically performed, with respect to "button determination", the threshold values for the right answer rate/reaction time (average value, standard deviation value)/reaction frequency under the resting task are set under a predetermined condition as shown in FIG. 4A. Furthermore, with respect to "microphone determination", the threshold values for the utterance speed and the utterance magnitude are set. When the shift is based on a measurer's manual operation, the shift can be performed at any timing. The threshold values may be input and set in consideration of the average values, the maximum values, the minimum values, etc. of various kinds of feature amounts recorded in the database of the stimulating task presentation controller 100. Any one of "button determination" and "microphone determination" can be selected as the task used for the shift determination. With respect to the right answer rate, a wrong answer rate which is opposite to the right answer rate may be recorded or displayed. Each parameter may be changed while checking a response result to the presentation of a task displayed on the display unit 120.

Next, presentation method and frequency of the stimulating task are set on the input/setting screen of the stimulating task generating parameters in the stimulation parameter setting unit 103 of FIG. 4B. In this example, any one of "feedback occurrence", "random occurrence" and "manual occurrence" can be selected. In "feedback occurrence", the task presentation is automatically set by using the right answer rate and the reaction time under the resting task or the stimulating task on a real-time basis. For example, when the button push right answer rate and the reaction time under the resting task or the stimulating task are good and the task is easy for the examinee, the presentation time may be set to be rather short and thus the degree of difficulty may be enhanced. Furthermore, when the word recall number under the stimulating task is small, an initial letter containing a large number of words can be automatically presented so as to make the examinee concentrate on the task. In "random occurrence", the type and time of the stimulating task are randomly set. In "manual occurrence", the task type and time which are arbitrarily set by the operator are applied.

In "feedback occurrence" and "random occurrence", the task presentation time is adjusted on a real-time basis, however, the overall presentation time width of each task is adjusted to be constant. A value input in "stimulating task presentation time width" is used as the adjusted time width.

In the stimulating task presentation frequency, the execution frequency N2 of the stimulating task is input, and the resting task is automatically executed again after the stimulating task of the execution frequency is finished. In the second resting task, the stability degree parameters are also applied, and the measurement is finished at the time point when the threshold values are satisfied.

When the initialization is finished and the preparation of the measurement is completed, the first resting task is executed on the examinee (S504).

Subsequently, the feature amount of the examinee when the first resting task is executed is measured/recorded (S506). For example, in the case of "button determination", the reaction frequency is detected when the button is pushed. As examples of the right answer rate/reaction time (average value, standard deviation value), reaction frequency under the resting task, the right answer rate to the reaction frequency is determined as six times to 12 times/ten times to 20 times (60%). Furthermore, the reaction time (average value) until the button is pushed is set to (200 to 300 ms)/frequency=A, and the standard deviation value (variance) is determined as follows.

$$((A1-A)2+(A2-A)2, \ldots, +(An-A)2)/N = 100 \text{ to } 150 \text{ ms}$$

Furthermore, when the resting task is "microphone determination", as the threshold value for the utterance speed of the examinee, the time interval from the peak value to the next peak value of the voice waveform is set to 1000 ms±100 ms. This waveform value is measured by an accelerometer, for example. The magnitude of utterance is set to 20 dB to 30 dB, and the waveform is observed by visual sense, for example.

Subsequently, it is determined whether the degree of stability of the examinee is high or not (S508). This is performed by comparing the measurement value with a preset threshold value. When the response value of the examinee satisfies this threshold value and the stability degree is determined to be high, it is determined whether the stimulating task should be changed or not (S516). When the stimulating task is changed, for example, the presentation time of the task is shortened to increase the level of the stimulating task (S518).

Figure 6:
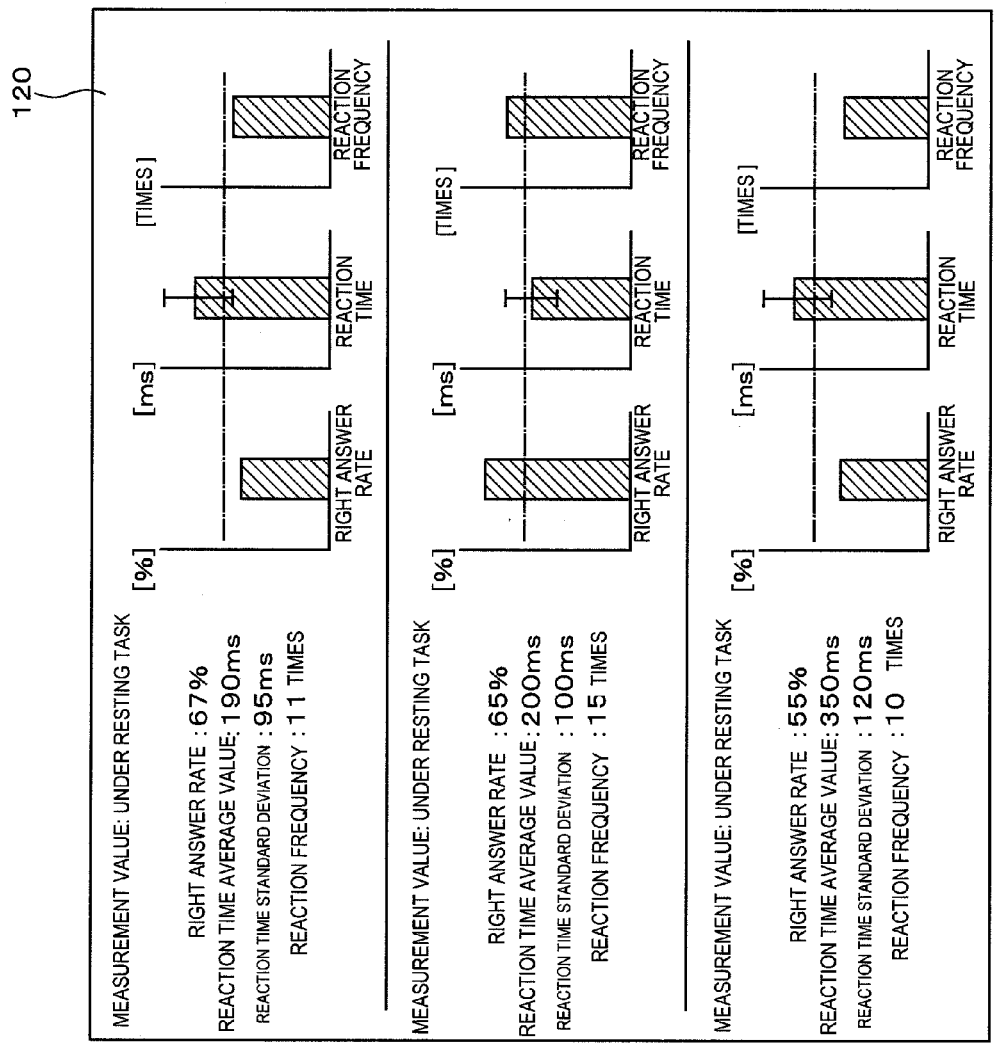
FIG. 6 shows a screen on which right answer rate/reaction time (average value, standard deviation value)/reaction frequency under measurement in each examination state are displayed by numerical values and graphs.

FIG. 6 shows a screen on which the right answer rate, reaction time (average value, standard deviation value)/reaction frequency under measurement in each examination state are displayed by numerical values and graphs. The numerical values and the graphs are updated and displayed on a real-time basis in conformity with the task reaction under measurement. Broken lines in FIG. 6 represent the threshold values of the resting task or the standard values of the stimulating task. With respect to the right answer rate and the reaction frequency, the upper side above the broken line clears the threshold value or the standard value, and with respect to the reaction time, the lower side below the broken line clears the threshold value or the standard value.

Conversely, when it is determined that the stability degree is low (S508), the resting task is repeated until the predetermined frequency N1 (S510), and the processing waits until the examinee is stabilized.

The upper stage of FIG. 6 shows a state that the resting task is executed on the examinee, and each of the right answer rate, the reaction time and the reaction frequency does not reach the threshold value. Accordingly, in this case, it is determined that the stability degree is low. On the other hand, the middle stage of FIG. 6 shows a state that the resting task is likewise executed. However, each of the right answer rate, the reaction time and the reaction frequency clears the threshold value. Accordingly, in this case, it is determined that the stability degree is high.

When the stability degree of the examinee is still low although the resting task is repeated until the predetermined frequency N1, it is determined whether the measurement should be stopped or not (S512). When the stability degree is remarkably low, the measurement is stopped (S514), and the processing waits until the state is stabilized. When it is determined that the measurement can be continued although the stability degree is low, it is determined whether the stimulating task should be changed or not (S516). When the stimulation task should be changed, the stimulating task is changed to an easier one (S518), and then the stimulating task is executed (S520). With respect to a standard stimulating task, in the case of "button determination", the examinee is supplied with a task of randomly changing the position of the button or the time interval and then pushing the button. Furthermore, in the case of "microphone determination", the examinee is supplied with a word recall task, for example, a task of successively uttering only plural words starting from "a". When the stimulating task is changed to an easier task than the standard task, the interval of the presentation time of the task is lengthened, for example.

Subsequently, the feature amount of the examinee during the execution of the stimulating task is measured and recorded (S522). The lower stage of FIG. 6 shows a state that the stimulating task is executed on the examinee, and each of the right answer rate, the reaction time and the reaction frequency does not reach the standard value.

Likewise, the execution of the first resting task and the stimulating task is repeated at the predetermined frequency (N2) (S504 to S524). Thereafter, the second resting task is executed (S526), and the feature amount of the examinee is measured and recorded (S528). The second resting task has the same content as the first resting task, and only the execution time thereof is different. Then, it is determined whether the stability degree of the examinee is high or not (S530). When the state of the examinee is stable, the task is finished. When the state of the examinee is not stable, the second resting task is executed on the examinee again, and the feature amount of the examinee is measured and recorded (S526, S528).

It is desirable that the stimulating task is executed after the stimulating task is changed to an easier one (S518), and when a result indicating that the stability degree of the examinee is high with respect to the second resting task is obtained, the task is not directly finished and the processing returns to the step of changing the stimulating task (S516) to return the stimulating task to the standard stimulating task (S518) and performs the measurement again.

Figure 7:
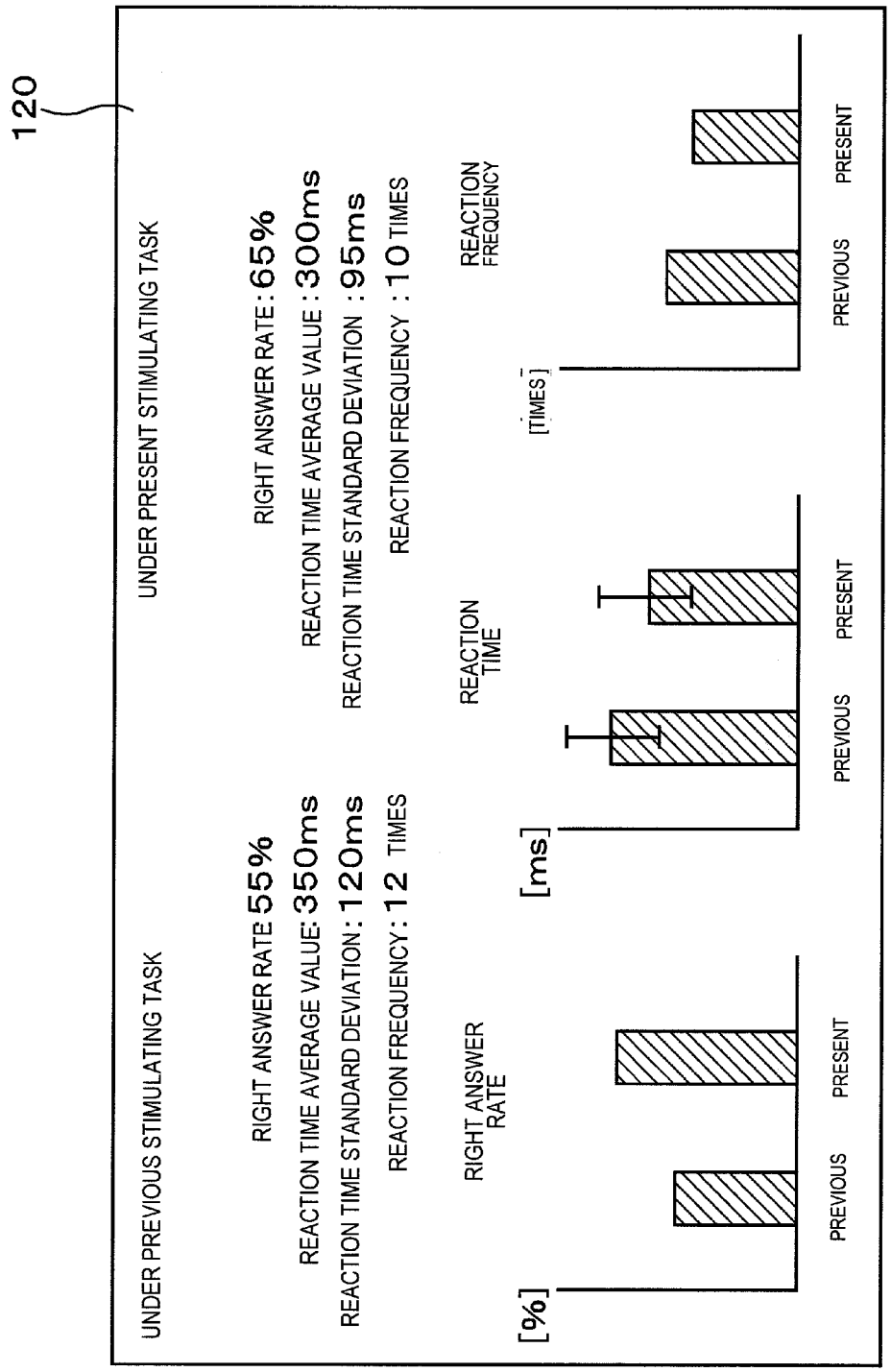
FIG. 7 shows a screen on which the right answer rate/reaction time (average value, standard deviation value)/reaction frequency of the same examinee to the same stimulating task which are stored in the database are comparatively displayed.

FIG. 7 shows a screen on which the right answer rate/reaction time (average value, standard deviation value)/reaction frequency of the same examinee to the same stimulating task which are recorded in the database are displayed for comparison. As compared with the previous measurement, the present measurement is improved in right answer rate and reaction time, however, the reaction frequency is lowered. By the comparative display as described above, the difference in performance to the stimulating task between the previous examination and the present examination can be easily considered.

Figure 8A:
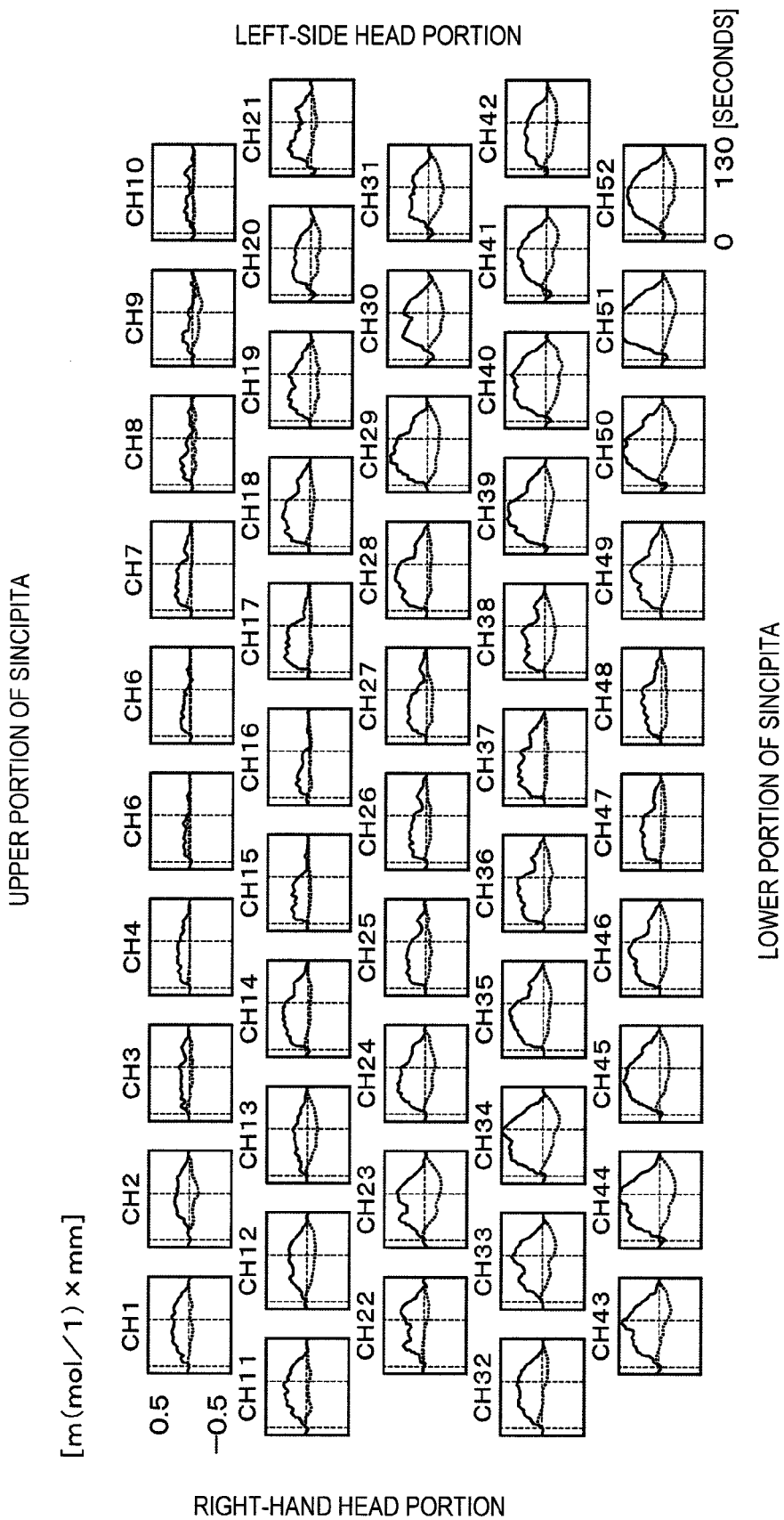
FIG. 8A shows hemoglobin variation waveform of cerebral cortex when a word recall task is executed in the arrangement of measurement channels (CH1 to CH52) of FIG. 3 under a state that the state under resting task is stabilized.
Figure 8B:
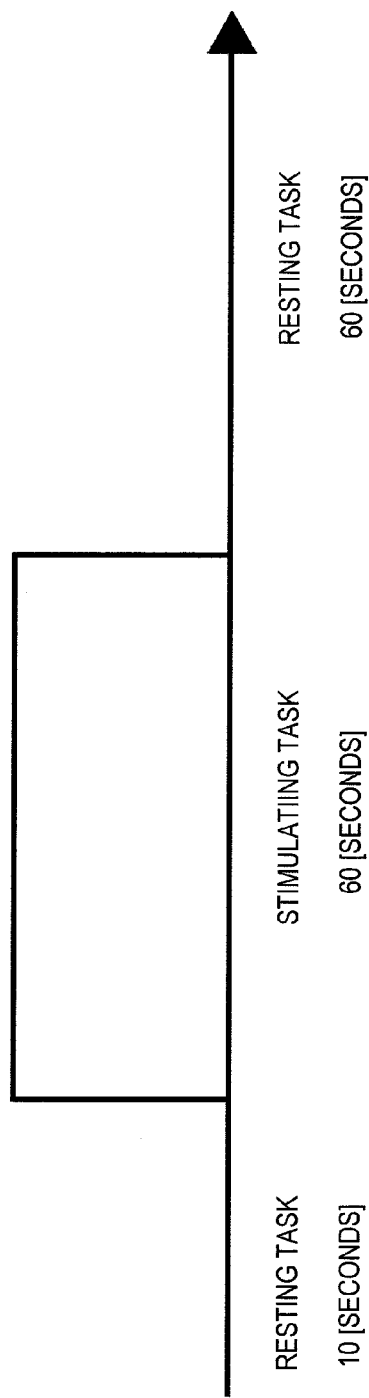
FIG. 8B is a diagram showing time patterns of a first resting task, a stimulating task and a second resting task which are executed under the measurement of FIG. 8A.

FIG. 8 (FIG. 8A, FIG. 8B) shows hemoglobin variation waveforms of cerebral cortex when the word recall task is executed in the arrangement of the measurement channels (CH1 to CH52) of FIG. 3. In this example, the first resting task (10 seconds), the stimulating task (60 seconds) and the second resting task (60 seconds) are executed with a time pattern shown in FIG. 8B, and this processing is repeated at three times with the same time pattern, and the average values thereof are calculated and shown in FIG. 8A. A solid line in each measurement channel (CH1 to CH52) of FIG. 8A represents oxygenated hemoglobin and a dashed line represents reduced hemoglobin. This waveform is an example in which the stimulating task is presented under a state that the examination condition under the first resting task is stable, that is, under a state that the stability degree of the examinee is determined to be high in S508 of FIG. 5. There is observed a pattern in which oxygenated hemoglobin increases simultaneously with the start of the stimulating task, and it decreases with time under the second resting task after the stimulating task is finished.

Figure 9A:
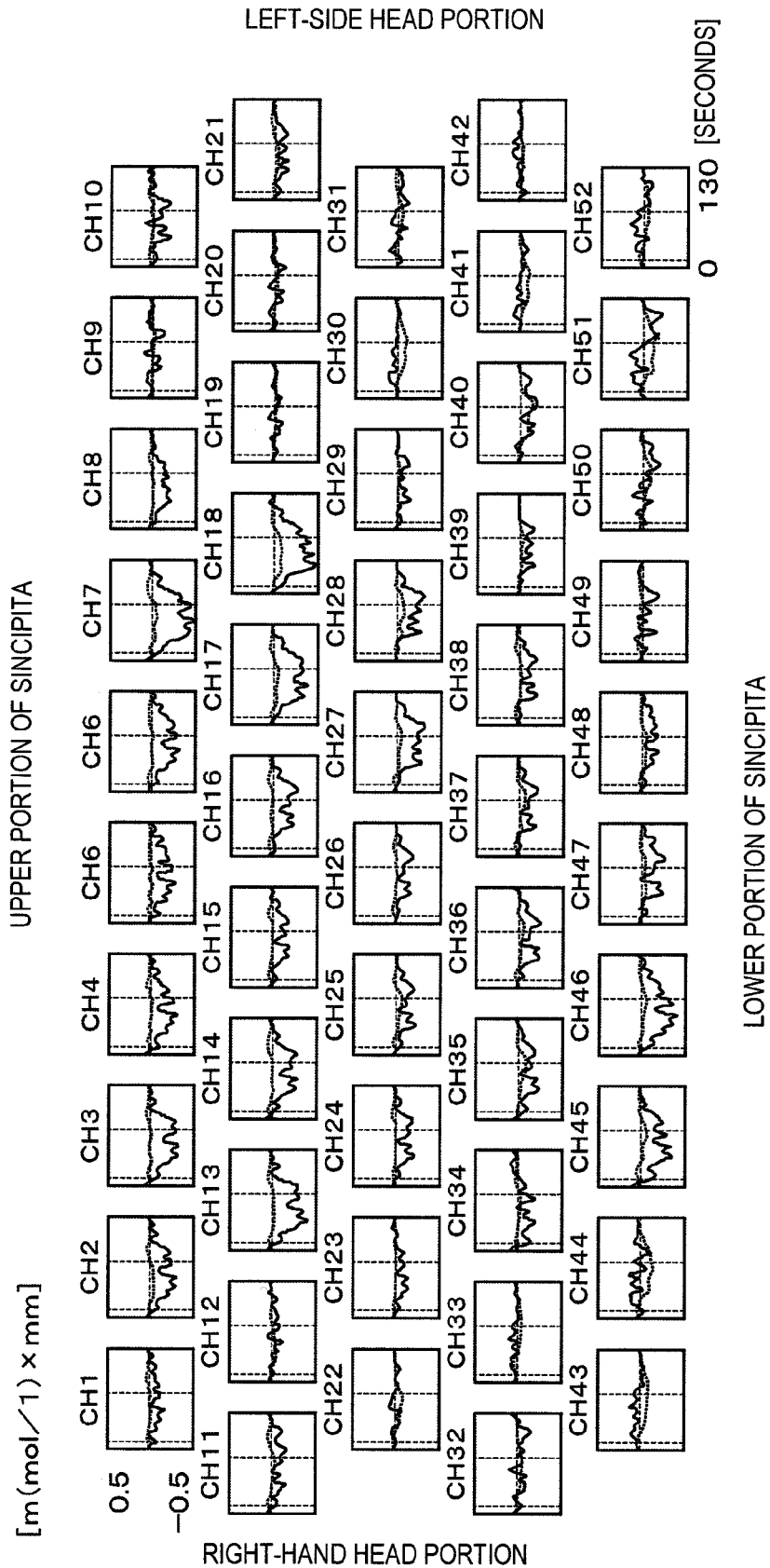
FIG. 9A shows hemoglobin variation waveform of cerebral cortex when a word recall task is executed as in the case of FIG. 8 under a state that the state under resting task is not stabilized.
Figure 9:
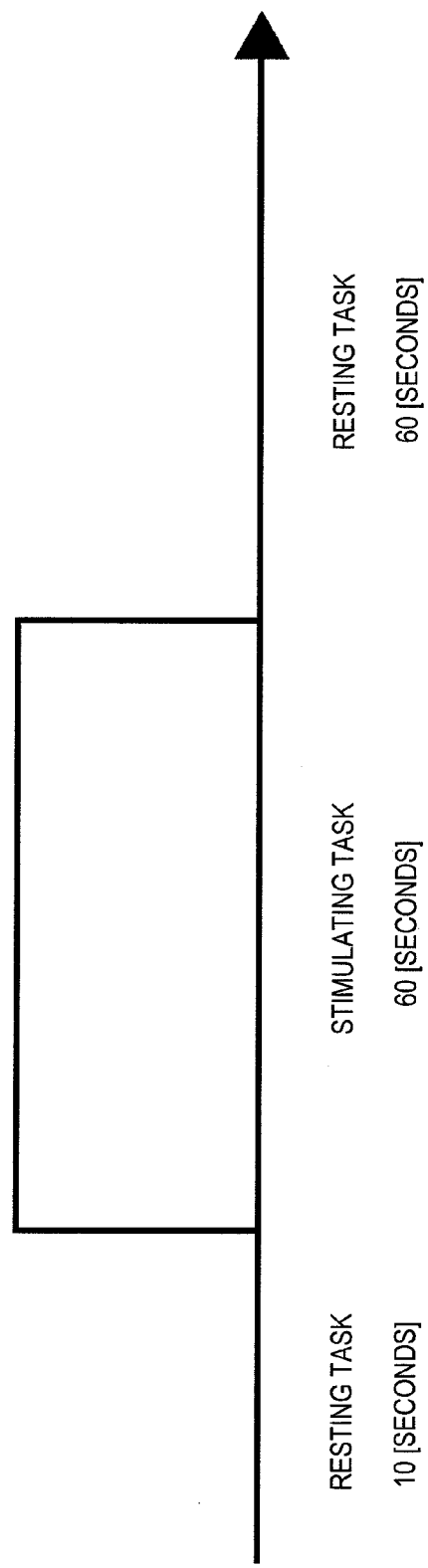
FIG. 9B is a diagram showing time patterns of the first resting task, the stimulating task and the second resting task which are executed under the measurement of FIG. 9A.

Furthermore, FIG. 9 (FIG. 9A, FIG. 9B) shows hemoglobin variation waveforms of cerebral cortex when the word recall task is executed as in the case of FIG. 8. That is, the first resting task, the stimulating task and the second resting task are executed with a time pattern shown in FIG. 9B, and this processing is repeated at three times, and the average values thereof are calculated and shown in FIG. 9A. This waveform is an example in which the stimulating task is presented under a state that the examination condition under the first resting task is unstable, that is, a state that the stability degree of the examinee is determined not to be high in S508 of FIG. 5. There is observed a pattern in which oxygenated hemoglobin decreases simultaneously with start of the stimulating task, and increases after the stimulating task is finished. It is considered that this occurs because the brain activity increases because the examination condition under the first resting task is unstable and conversely the brain activity is lowered under the stimulating task. This result is one of events representing that the stability degree of the first resting task is important.

In the invention, when it is determined in S508 of FIG. 5 that the stability degree of the examinee is not high, the execution of the resting task is repeated. In other words, the stability degree under the first resting task is enhanced or the level of the stimulating task is lowered by lengthening the execution time of the first resting task. As described above, the stimulating task is examined under the state that the examinee is stable, so that the situation as shown in FIG. 9 can be avoided and proper measurement data can be obtained.

Second Embodiment

Figure 10B:
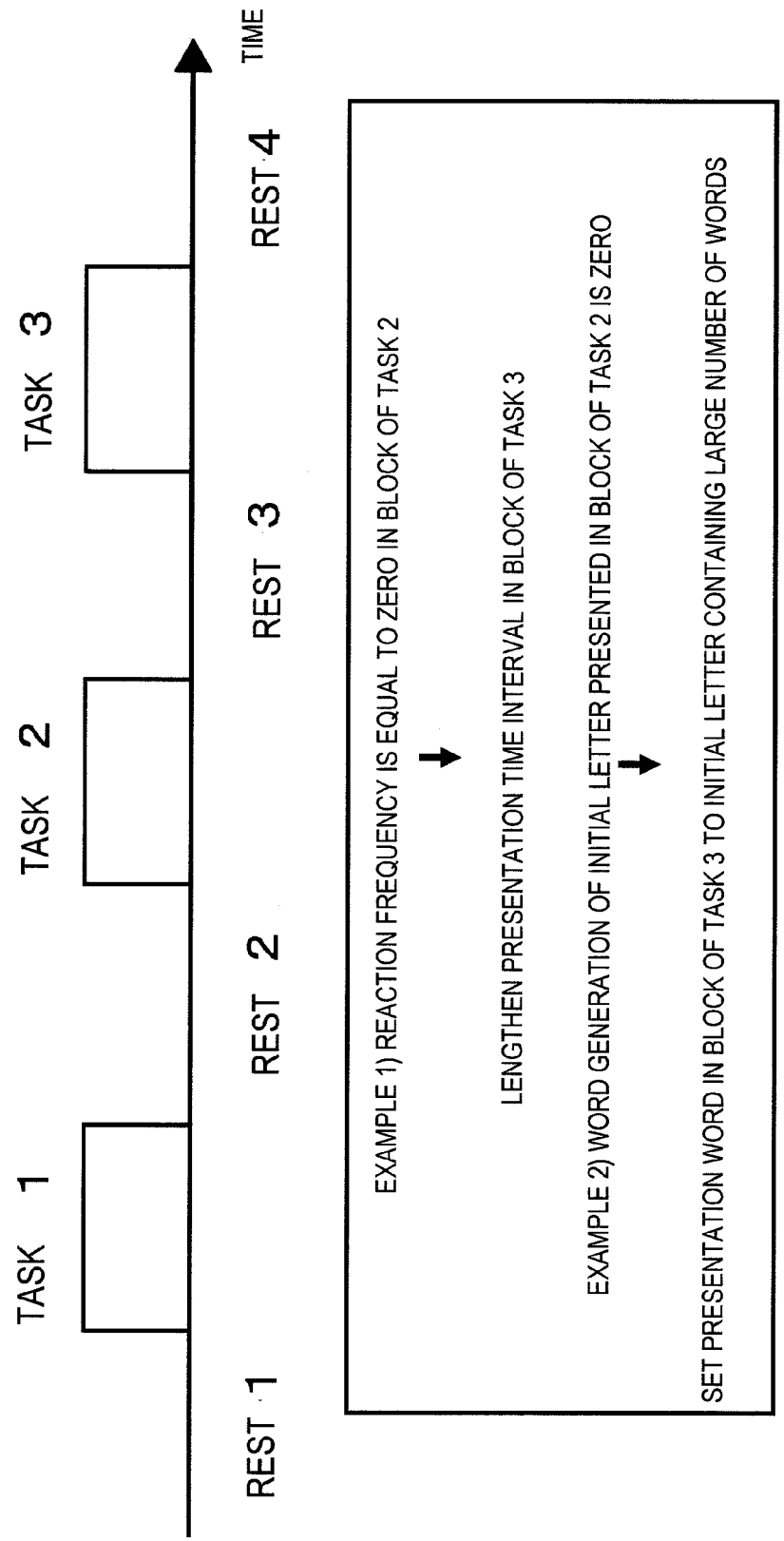
FIG. 10B is a diagram showing the processing of the resting task and the stimulating task which is another embodiment of the invention.

Another embodiment of the invention will be described with reference to FIG. 10 (FIG. 10A, FIG. 10B). In these examples, take-in of the resting task and the stimulating task and change of the contents thereof are successively performed on the basis of the measurement result. First, in the example of FIG. 10A, a task block representing an improper reaction is deleted on the basis of the average (in-task) value of the whole displayed on the display unit 120 of the stimulating task presentation controller 100. That is, the resting task (rest 1, rest 2, rest 3) and the stimulating task (task 1, task 2, task 3) are alternately and repeatedly executed on the examinee under measurement every 60 seconds according to the same method as described in the first embodiment, and obtained data are successively checked on the display unit 120 of the stimulating task presentation controller 100. As a result, it is assumed that the reaction frequency of the examinee is equal to zero in the block of the task 2, for example. In this case, it is considered that the examinee cannot concentrate on the task and thus the right answer rate is temporarily equal to zero. Therefore, the measurement is not finished at three times, a resting task 4 and a stimulating task 4 are further executed on the examinee, and the data of the block of the task 2 in the obtained data is excluded from an analysis target. Through the processing as described above, more proper measurement data can be obtained.

Next, in an example of FIG. 10B, the content of the next task is adjusted by using the value of the determination parameter in the task block. That is, the resting task (rest 1, rest 2, rest 3) and the stimulating task (task 1, task 2, task 3) are alternately and repeatedly executed on the examinee under measurement every 60 seconds according to the same method as described in the first embodiment, and obtained data are successively checked on the display unit 120 of the stimulating task presentation controller 100. As a result, it is assumed that the reaction frequency of the examinee is equal to zero in the block of the task 2, for example. In this case, it is considered that the examinee answers in a mad rush and thus the right answer rate is temporarily equal to zero. Therefore, the interval of the presentation time of the task in the block of the next task 3 is lengthened, whereby the examinee can answer slowly. Or, it is assumed that the word generation of an initial letter presented in the block of the task 2 is equal to zero. In this case, the presented word in the block of the task 3 is changed to an initial letter containing many words. Through the processing as described above, more proper measurement can be performed in accordance with the state of the examinee.

Third Embodiment

A third embodiment of the state stability degree under the resting task according to the invention will be described with reference to FIG. 11.

Figure 11:
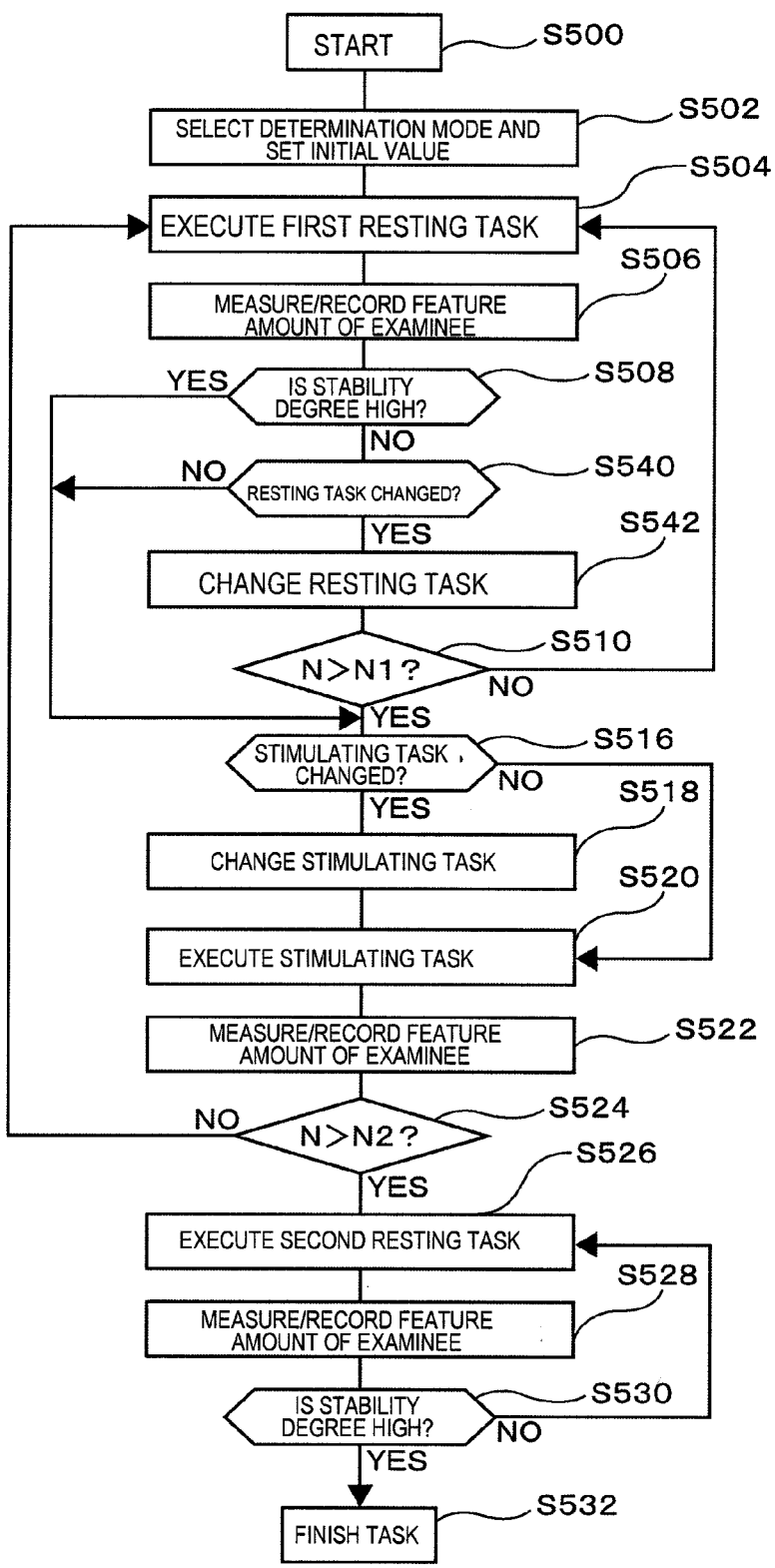
FIG. 11 is a diagram showing a flowchart of stimulating task presentation implementing "degree of state stability under resting task" in a third embodiment of the invention.

FIG. 11 is a flowchart of the stimulating task presentation implementing "state stability degree under resting task" in the third embodiment of the invention. As a different point from the first embodiment, before the processing shifts to the stimulating task, the resting task is repeated at a predetermined frequency, for example, at three times, it is determined in accordance with the state of the stability degree of the examinee in this repeat process whether the resting task should be changed or not (S540), and the resting task is changed to an easier one than the standard resting task when it is determined that the stability degree is low and thus the change is necessary (S542). For example, the interval of the presentation time of the task is lengthened. Accordingly, more proper processing can be performed to keep resting state in accordance with the state of the examinee.

The invention can be applied to not only the device for measuring the brain function of the examinee by the optical topography device 130, but also an examinee's function measuring device for examining the function of muscle of the examinee, for example.

DESCRIPTION OF REFERENCE NUMERALS

100 stimulating task presentation controller, 101 rest parameter setting unit, 102 resting task memory/database, 103 stimulation parameter setting unit, 104 stimulating task memory/database, 105 task presentation controller, 106 analyzer, 107 comparator, 110 stimulation presenting unit, 112 microphone, 114 button, 120 display unit, 130 optical topography device

The invention claimed is:

1. A stimulating task presentation device in a living body optical measurement device comprising:
    a stimulation presenting unit configured to present a stimulation to an examinee;
    a brain function measuring device configured to measure a brain function of the examinee in parallel to the presentation of the stimulation; and
    a stimulation presentation controller configured to control the stimulation presented by the stimulation presenting unit, wherein the stimulation presentation controller includes:
        a setting means configured to set a resting task and a stimulating task to be presented to the examinee;
        a detecting means configured to detect a response of the examinee to the resting task and the stimulating task; and
        a task presentation control means configured to determine whether or not a sufficient degree of stability exists for a parameter, on the basis of the detected response when the resting task is presented, and configured to control the presentation of the resting task or the stimulating task on the basis of the determination of whether or not a sufficient degree of stability exists for a parameter, wherein said degree of stability is of at least one parameter selected from: utterance reaction time, utterance frequency, right answer rate, reaction time average value, reaction time standard deviation, and reaction frequency.

2. The stimulating task presentation device in the living body optical measurement device according to claim 1,
    wherein the stimulation presentation controller has a threshold value setting means configured to set a threshold value used to determine whether or not the degree of stability is sufficient when the resting task is presented; and
    wherein the task presentation control means is configured to determine, on the basis of a comparison result between the detected response and the threshold value, whether the degree of stability when the resting task is presented is above, below, or equal to the threshold value.

3. The stimulating task presentation device in the living body optical measurement device according to claim 1, wherein the resting task contains a first resting task prior to the stimulating task, and a second resting task that is continuously presented with the stimulating task, and the task presentation control means is configured to determine whether or not the degree of stability is sufficient when the first resting task is presented.

4. The stimulating task presentation device in the living body optical measurement device according to claim 1, wherein the stimulation presentation controller has a database for holding plural preset values relating to the resting task.

5. The stimulating task presentation device in the living body optical measurement device according to claim 2, wherein the task presentation control means is configured to control a shift to presentation of the stimulating task when the degree of stability is not below the threshold value.

6. The stimulating task presentation device in the living body optical measurement device according to claim 2, wherein the task presentation control means is configured to control a repeat of presentation of the resting task when the degree of stability is below the threshold value.

7. The stimulating task presentation device in the living body optical measurement device according to claim 2, wherein the task presentation control means is configured to control a lowering of level of the stimulating task when the degree of stability is below the threshold value.

8. A stimulating task presentation method in a living body optical measurement device that includes a stimulation presenting unit configured to present a stimulation to an examinee, a brain function measuring device configured to measure a brain function of the examinee in parallel to the presentation of the stimulation, and a stimulation presentation controller configured to control the stimulation presented by the stimulation presenting unit, the method comprising:
    setting a resting task and a stimulating task to be presented to the examinee;
    detecting a response of the examinee to the resting task and the stimulating task;
    determining whether or not a degree of stability is sufficient, on the basis of the detected response when the resting task is presented; and
    controlling presentation of the resting task or the stimulating task on the basis of the determination of whether or not a sufficient degree of stability exists;
    wherein said degree of stability is of at least one parameter selected from: utterance reaction time, utterance frequency, right answer rate, reaction time average value, reaction time standard deviation, and reaction frequency.

9. The stimulating task presentation device in the living body optical measurement device according to claim 2, wherein the determination of whether or not the degree of stability is sufficient includes: comparing between the detected response and a threshold value, and determining whether or not the degree of stability when the resting task is presented is above, below or equal to the threshold value.

10. The stimulating task presentation device in the living body optical measurement device according to claim 1,
    wherein said degree of stability is of a parameter selected from the group consisting of: utterance reaction time and utterance frequency.

11. The stimulating task presentation method in the living body optical measurement device according to claim 8,
    wherein said degree of stability is of a parameter selected from the group consisting of: right answer rate, reaction time average value, reaction time standard deviation, and reaction frequency.

12. The stimulating task presentation device in the living body optical measurement device according to claim 1, wherein said degree of stability is of a parameter selected from the group consisting of: utterance reaction time and utterance frequency.

13. The stimulating task presentation method in the living body optical measurement device according to claim 8, wherein said degree of stability is of a parameter selected from the group consisting of: right answer rate, reaction time average value, reaction time standard deviation, and reaction frequency.

* * * * *